United States Patent
Vaudrey et al.

(10) Patent No.: US 6,532,296 B1
(45) Date of Patent: Mar. 11, 2003

(54) ACTIVE NOISE REDUCTION AUDIOMETRIC HEADPHONES

(76) Inventors: Michael Allen Vaudrey, 208 Northlake Rd., Columbia, SC (US) 29223; William Richard Saunders, 2509 Plymouth St., Blacksburg, VA (US) 24060

( * ) Notice: Subject to any disclaimer, the term of this patent is extended or adjusted under 35 U.S.C. 154(b) by 0 days.

(21) Appl. No.: 09/123,973

(22) Filed: Jul. 29, 1998

(51) Int. Cl.[7] .............................................. H04R 25/00
(52) U.S. Cl. ........................ 381/371; 381/71.6; 73/585
(58) Field of Search ...................... 381/60, 320, 71.6, 381/370, 371; 73/585; 600/559

(56) References Cited

U.S. PATENT DOCUMENTS 4,079,198 A * 3/1978 Bennett ...................... 600/559
4,759,070 A * 7/1988 Voroba et al. ................ 381/60
5,771,298 A * 6/1998 Davis et al. .................. 381/60
5,825,894 A * 10/1998 Shennib ....................... 381/60
6,139,507 A * 10/2000 Jeng ........................... 600/559

FOREIGN PATENT DOCUMENTS

JP        10085202 A   *  4/1998

* cited by examiner

Primary Examiner—Forester W. Isen
Assistant Examiner—James Hiney

(57) ABSTRACT

Active noise reduction headphones for audiometry where the earphone portion of said headphones has a cavity volume greater than 6 cc and including an acoustic-electric sensing means and an electro-acoustic transducing means which are used cooperatively and which has additional passive noise control means in the form of a circumaural seal around the ear for improving high frequency noise control performance, the headphone having a summing junction for combining the active noise reduction signal and an audiometry test signal.

12 Claims, 7 Drawing Sheets

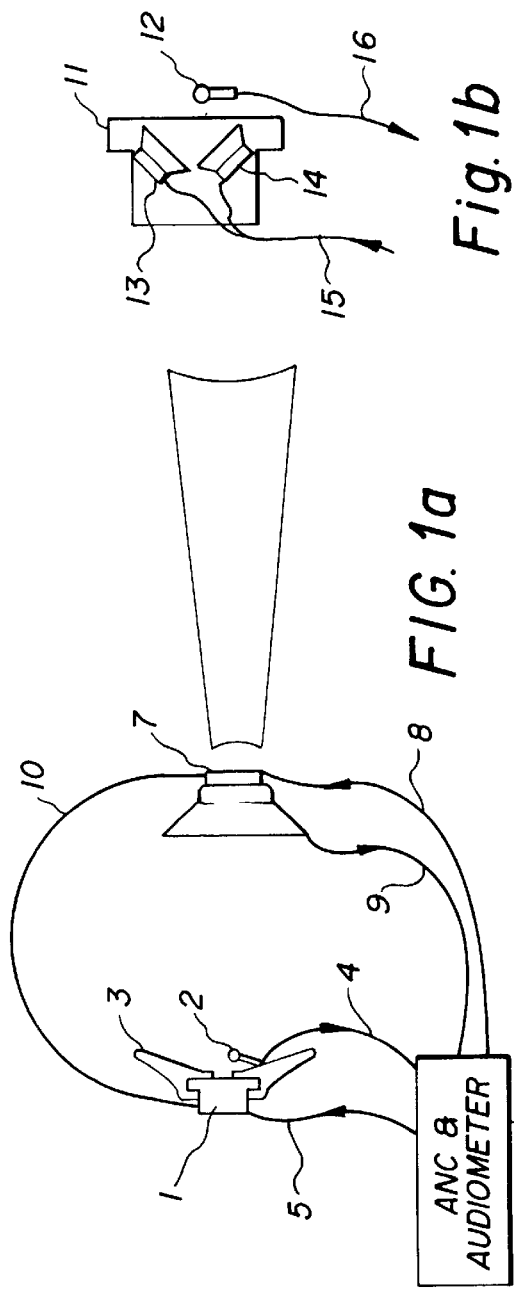
FIG. 1a
FIG. 1b
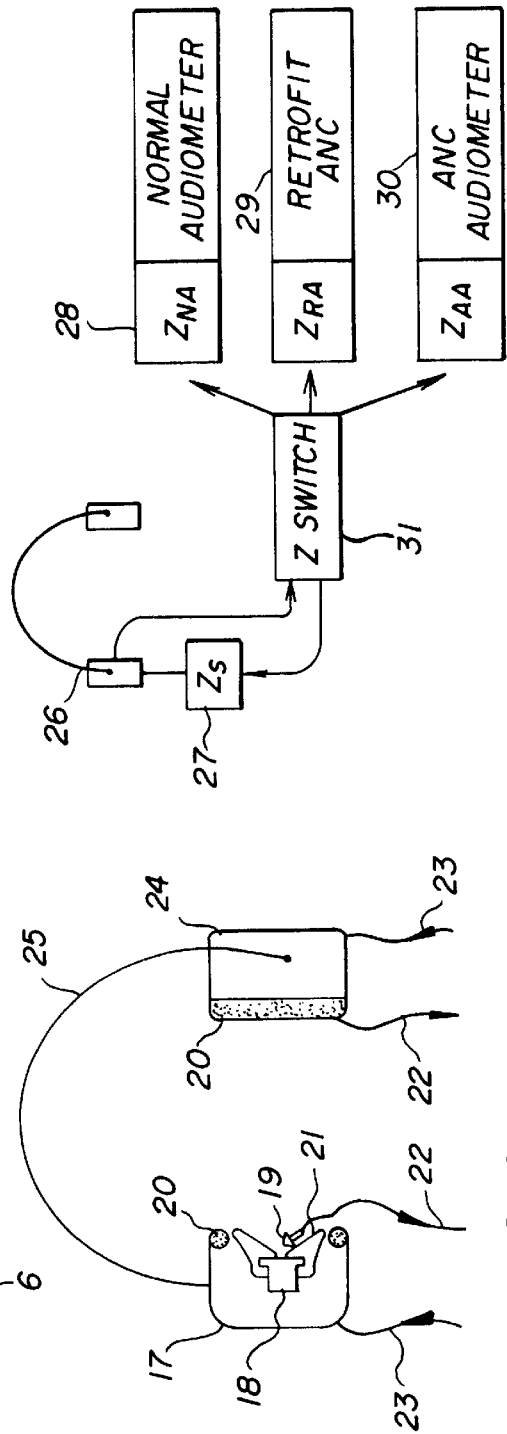
FIG. 2
FIG. 3

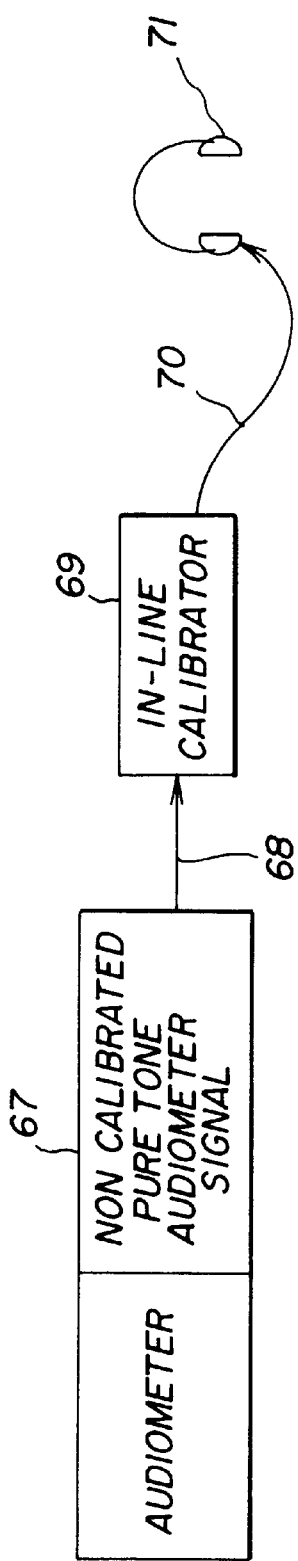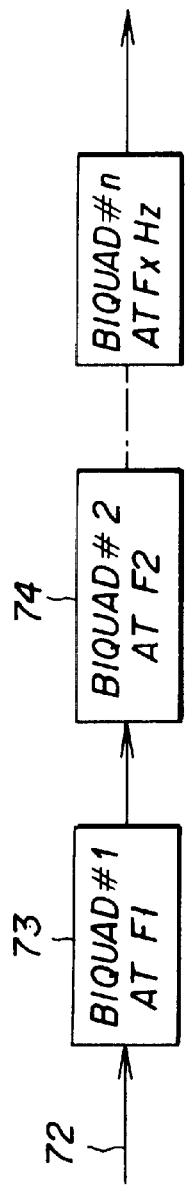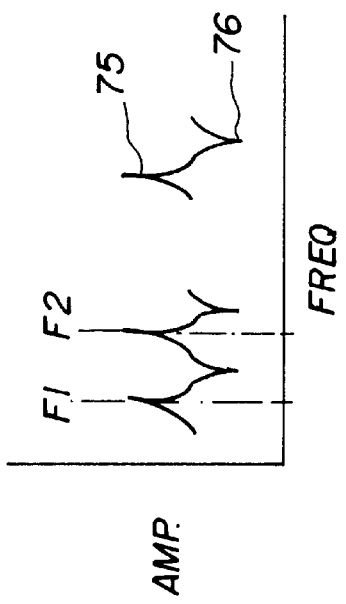
FIG. 8a
FIG. 8b
FIG. 8c

ACTIVE NOISE REDUCTION AUDIOMETRIC HEADPHONES

FIELD OF THE INVENTION

This invention relates to the use of an audiometry headphone system utilizing an acousto-electric transducer for the purpose of implementing active noise control during and in conjunction with audiometry testing. Since the process of some embodiments of active noise control alter the audiometry test stimulus, methods for correcting that alteration are also covered. Details of the inventions include passive control measures used in conjunction with ANR audiometer headphones, calibration procedures, and ANR headphone design provisions for alternative ANR audiometer configurations. The invention also describes several new and unique methods for calibrating both standard and ANR audiometry headphones. A calibration process which occurs external to the audiometer and that is integrated into the headphone or the headphone wiring mechanism will operate with a standard headphone or a special configuration of the ANR audiometer headphone. An alternative manual or automatic calibration procedure is also presented that utilizes the ANR error microphone instead of the more traditional calibration fixture.

PRIOR ART

The field of audiometry is somewhat arcane with not many developments having occurred in the recent past. Of note are several U.S. patents dealing with the general field. A recent patent to Isenhath, U.S. Pat. No. 4,991,219 discloses a chamber in which subjects are tested with novel positioning of speakers. The 26 year old patent to Arguimbau et al, U.S. Pat. No. 3,647,968 discloses the use of a masking signal in the ear of the subject opposite the one being tested and is correlated to the test signal. Shennib, U.S. Pat. No. 5,197,332 discloses the use of headphones in audiometry but the headphones disclosed are not noise cancelling type. Feezor discloses a portable audiometry enclosure with noise masking in the ear not being tested. The patent to Zwicker, U.S. Pat. No. 4,390,748, discloses the use of frequency band filters in headphones for audiometry purposes.

Other pertinent U.S. Patent disclosures are found in U.S. Pat. Nos. 3,648,196; 3,793,484 and 485; 3,809,811; 4,109,106; 4,224,468; and 4,768,165. It is noteworthy that none of the prior art discloses the use of noise attenuation circuitry in audiometry or the use of the specific switching circuitry disclosed herein.

OBJECTS OF THE INVENTION

Accordingly, it is an initial object of this invention to provide an audiometry headphone system that is capable of operating in conjunction with an integrated ANR audiometer or a retrofit ANR audiometer, and It is another object of this invention to provide an ANR audiometry headphone system that utilizes an acousto-electric sensor to deliver a measure of the sound pressure level to or from the controller portion of the ANR audiometer or retrofit device, and It is yet another object of this invention to provide an audiometry headphone system capable of reducing the ambient noise in the vicinity of the test subject's ear during and in conjunction with audiometric testing, and It is a further object of this invention to incorporate additional passive noise control measures to be used in conjunction with the active components of the ANR audiometry headphones, and It is a still further object of this invention to use one or multiple actuators to deliver the active noise control signal and the audiometry test stimulus or any combination thereof, to the test subject's ears, and Another object of this invention is to provide a means by which ANR audiometry headphones can be used with a variety of audiometer types including standard audiometers, retrofit ANR audiometers, and integrated ANR audiometers each having different types of outputs ranging from combined control and calibrated test stimulus to separate control and calibrated test stimulus to separate control and non-calibrated test stimulus, and Yet another object of this invention is to provide a means for calibrating the ANR audiometer headphones in such a manner that the current ISO and ANSI standards are still adhered to, and A further object of this invention to provide non-standard ways and means for calibrating ANR audiometer headphone designs and configurations that may not fall within the specified regulations for audiometry, and Furthermore, another object of this invention to use hardware or software located external to the audiometer for the purpose of calibrating any type of standard or non-standard audiometry headphones, and An additional object of this invention to provide multiple ways of using analog hardware, digital software, or the combination of the two to perform the calibration process, and An added object of this invention is to provide a calibration technique that does not require modification of conventional audiometer hardware as the technique has calibration hardware or software built into the audiometry headphones themselves, and Another object of this invention is to use the ANR audiometer headphones sensing device in order to perform calibration of the ANR audiometer headphones with or without the aforementioned calibration process, and And finally, it is an object of this invention to provide both semi-automated and fully-automated calibration processes for both the standard audiometry headphones and the ANR audiometry headphones.

BRIEF DESCRIPTION OF THE FIGURES

FIG. 1a illustrates one possible generalized form of the ANR headphones for audiometry with one earphone in cutaway view and the other in full profile view. FIG. 1b illustrates one possible arrangement of the electro-acoustic transducer incorporating two separate transducers, one for the audiometer signal and one for the control signal.

FIG. 2 illustrates one form of the ANR headphones for audiometry which incorporates passive ambient noise control measures in addition to the active noise reduction, built into the same headphone system.

FIG. 3 illustrates a general arrangement for an ANR headphone system for audiometry that permits it to be used in several different hardware configurations including: a normal audiometer, a retrofit ANR audiometer and an integrated ANR audiometer.

FIG. 4a shows the necessary inputs and outputs of the ANR headphones for audiometry when the ANR audiometer electronically calibrates and combines the audiometer signal and the control signal so only a left and right electro-acoustic transducer force is required. FIG. 4b illustrates the wiring required when the audiometer output includes both control and calibrated audiometer signal. FIG. 4c illustrates the same case when no audiometer signal calibration is performed.

FIG. 8 outline several alternative ways to calibrate audiometer headphones as well as ANR audiometer headphones. FIG. 8a illustrates the general arrangement of the in-line calibration hardware. FIG. 8b illustrates an in-line calibration configuration for pure tone audiometers. FIG. 8c illustrates one frequency response function of the hardware in FIG. 8b.

DETAILED DESCRIPTION AND PREFERRED EMBODIMENT

Figure 4C:
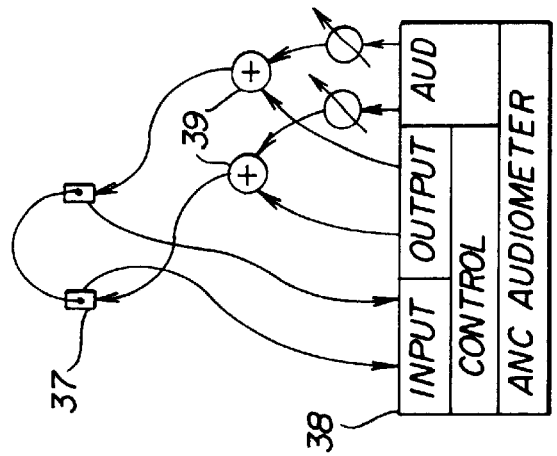
FIGS. 4a, 4b, and 4c illustrate three arrangements of the ANR headphones for audiometry used and configured for three different ANR audiometer designs.

Advances in digital signal processing and knowledge of local and global noise control approaches have caused active noise control (ANR) to take a more prominent stance in state-of-the-art technology. Specifically, active noise reduction (ANR) headphones have become commonplace technology for the purpose of hearing protection. Low frequency disturbing noise is the easiest target for ANR headphones because the zone of silence for low frequencies is quite large and the passive control provided by the circumaural cups housing the ANR actuator, is ineffective for low frequencies.

Low frequency noise disturbances are also a problem in audiometry testing. ANSI and OSHA requirements for ambient noise in the vicinity of audiometry testing are quite stringent, the reason being that the threshold for hearing can shift upward due to the presence of ambient noise in the test environment. This is of primary concern for individuals who must pass hearing tests in order to continue working, as well as clinicians who must provide a quiet environment for audiometry testing. Until very recently, state-of-the-art disturbance rejection for audiometry was limited to passive measures, the most effective and commonplace of them being the audiometry test booth. This invention discloses that it is possible to reduce low frequency ambient noise during an audiometry test to provide more accurate audiograms in the presence of excessive ambient noise.

In performing ANR for any application, it is critical to understand, and if possible design, the entire "system". For ANR headphones in general, the system consists of the input to the speaker, the air inside the dome, the wearer's ear, the enclosure dynamics of the circumaural dome, and the microphone measuring the sound pressure level (SPL) inside the dome. For ANR headphones designed for hearing protection, there are no standards for the shape and style for this system, the goal is simply to provide the best noise reduction possible from both active and passive measures. For standard audiometry testing, however, there are very strict rules currently in place governing the size, shape, and fit of audiometry headphones. Since the controller design so heavily depends on the system being controlled, and the audiometry headphone system is already strictly designed, several new innovations are required in order to incorporate active noise control into audiometry headphones, ensuring proper calibration, and system design.

The following descriptions and preferred embodiments are meant to encompass the use of headphones designed for the purpose of performing audiometry testing utilizing active noise control. In addition to this, many new innovations are described which pertain to the calibration of and calibration procedures for both standard audiometry headphones and especially ANR audiometer headphones. It is the thrust of this invention to focus on the system design of ANR audiometer headphones and their use with a wide range of configurations of audiometers, retro-fit ANR audiometers, and integrated ANR audiometers along with the calibration procedures for each case. Emphasis is not placed on the design and development of ANR controllers or audiometers for ANR audiometry. A secondary focus of this invention is toward explaining several new calibration techniques for both standard audiometer headphones and the claimed ANR audiometer headphones. The first is an in-line calibration technique circumventing the need to alter the audiometer calibration for either standard audiometer headphones or the new ANR audiometry headphones. The second is a technique, either manual or automated, to calibrate the ANR audiometer headphones using the error feedback sensor on the ANR headphones.

Standard or conventional audiometry headphones in use today must conform to very specific standards set forth in ISO 389 and ANSI S3.6. Currently, the most commonly used equipment that meets these specifications is the MX-41 style cushion coupled with the TDH style speaker from Telephonics. In many of the Figures and descriptions to follow, it is assumed that this configuration is taken as a starting point for meeting the specifications. Deviations from these products will be addressed throughout this discussion. FIG. 1a begins to develop a general deviation from this standard in order to form the ANR audiometer headphone. The left earphone shown in FIG. 1a is depicted as a cutaway version exposing the profile of the TDH type electro-acoustic actuator (1) and the MX style cushion (3). The headband (10) connects the left earphone/cushion assembly to the right assembly (7) not shown in section. The added feature to this standard audiometry headphone system is an acousto-electric transducer (2) placed in front of the speaker on both headphones. These transducers are used to measure the sound pressure level (SPL) inside the headphone near the ear during audiometry testing. This information is then relayed via wires (4)(9) to the active noise controller and audiometer subsystem (6). The audiometer then delivers the audiometry test stimulus and the anti-noise control signal back to the transducer(s) via separate wiring (5)(8). FIG. 1a is meant to represent the most generalized configuration of the ANR audiometry headphones. Conceivably, any transducer/actuator pair could be used to accomplish the same goal. From here on, alterations, additions, and modifications to this system are discussed in detail, without the loss of generality described above.

FIG. 1b illustrates one possible modification to the standard system described in FIG. 1a. Instead of using a single actuator for the right or left ear transducer, two separate transducers (13)(14) can be used. One can be intended for delivery of the audiometer test signal while the other can deliver the active noise control signal. The Figure illustrates that both actuators can be positioned inside the standard shaped casing (11) of the TDH actuator. The signals would then need to be delivered on separate wiring (15). In practice, this is unnecessary since the voltage signals for the audiometer signal and the control signal can be simply added to form a single voltage signal which can drive a single actuator. However, one practical implementation of this innovation may be applied to the case where an audiometer actuator already exists and the ANR audiometry headphones can be added to the existing system to permit ANR audiometry to occur without modification of the original audiometry actuator. An acousto-electric transducer 12 with feed wire 16 is also part of the system.

As mentioned earlier, an important element of current technology in ambient noise reduction for audiometry is passive noise control measures such as circumaural domes. Without deviating from ISO and ANSI standards, circumaural domes can be used to improve the performance of threshold tests by attenuating ambient noise. However, their improvement in performance over the standard audiometry headphone system is typically limited to frequencies above 1 kHz. Since active noise reduction headphone can be effective at attenuating frequencies below 1 kHz, it is important to incorporate the two measures together in order to ensure improved performance at all frequencies. FIG. 2 illustrates one possible arrangement of the ANR audiometry headphones that incorporate additional passive measures. The standard actuator (18) and cushion (21) are now attached within a circumaural dome (17) that meets the test subject's head with a cushion (20). The ANR headphones incorporate an acousto-electric transducer (19) to measure the SPL near the subject's ear. The passive control performance adds directly to the performance of the ANR, enhancing the overall performance. The added passive measure in FIG. 2 resembles a current product called the Audiocup. This passive measure mounts the speaker with a spring causing the MX style cushion (21) to contact the subject's head before the secondary Audiocup cushion (20). This allows the system to still meet the ISO and ANSI specifications. FIG. 2 is not meant to restrict the use of added passive measures in combination with ANR headphones for audiometry but rather include all types of passive measures, including the Audiocup style of circumaural earmuffs.

In the above discussion, it has been emphasized that the ANR audiometer headphones can be designed to work with ANR audiometers and still conform to the specified ISO and ANSI specification for audiometer headphones. It is also emphasized that new procedures and designs will be established that will permit new calibration techniques for ANR audiometer headphones that may not fit within the current guidelines but may outperform the standard audiometer headphone. Each of these issues pertain to the standard calibration procedure for audiometry headphones and designing the ANR audiometry headphones to either conform to the existing procedure or to establish a new one. In later paragraphs each of these cases is described in detail. However, before these issues are discussed in detail, the integration of the ANR headphone system with normal audiometers, ANR audiometers, and retro-fit ANR audiometers is described in detail.

Consider the generalized block diagram of FIG. 3. The ANR audiometer headphones (26) are depicted as a general earmuff arrangement without loss in generality provided in the previous discussions. (Future figures will also depict the ANR audiometry headphones as the general earmuff shape as in (26) with the same assumption). The electro-acoustic transducer, whether it's the TDH style or other, will have a certain input impedance (27) $Z_S$. In addition, the standard audiometer (28), is designed to drive a certain type of transducer, and thus has an output impedance $Z_{NA}$ that should couple with $Z_S$. Most normal audiometers are designed to drive the TDH-39P style speaker with a $Z_S$ of 10 ohms. Given the development of the ANR audiometry headphones and ANR audiometers, many other options exist. In fact, the TDH-39P does not have an ideal frequency response for ANR and will likely not be suitable as a transducer in the ANR audiometry headphones. Therefore, FIG. 3 illustrates an impedance switch (31) that will allow the impedance of the speaker to effectively change in the presence of various output devices such as the normal audiometer (28), retro-fit ANR audiometer (29), or integrated ANR audiometer (30). This device has an output impedance that matches that of the input impedance of the transducer built into the ANR audiometry headphones (be it the TDH-39P or other transducer). The input impedance to this switch, however, is changeable to meet the output impedance of the specified output device. In the case where all output devices ((28),(29),(30), etc.) have the same impedance and it matches that of $Z_S$, there is no need for an impedance switch (31). However, it is possible that some manufacturers will design a retro-fit ANR audiometer (29) or an integrated ANR audiometer (30) to match with a certain style of transducer that has an impedance $Z_S$ that is different from $Z_{NA}$. For the ANR audiometer headphones to continue to be useful with any normal audiometer, the impedance switching mechanism (31) is required.

Figure 4B:
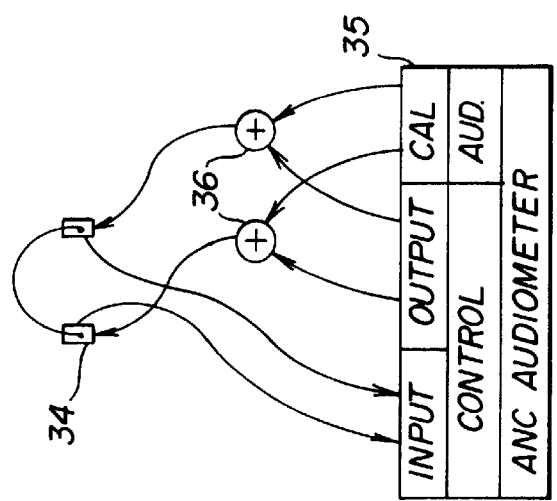
Figure 4A:
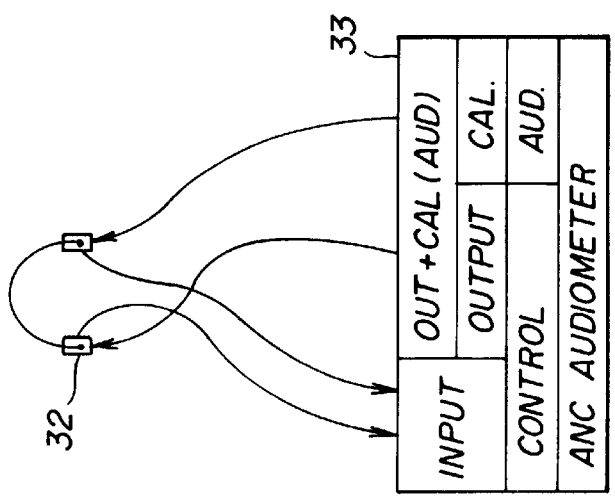

The next set of preferred embodiments focus on the transmission of signals from various forms of audiometers. FIGS. 4a, 4b, and 4c show three different ANR audiometer configurations which each require three different ANR audiometer headphone configurations. For each of the ANR headphone configurations described now, it is emphasized that the impedance switching mechanism described previously is still required (although not explicitly shown) if the ANR audiometer headphones are to work properly with audiometers that are designed with different output impedances. FIG. 4a is the first of three embodiments for an ANR audiometer and accompanying ANR audiometer headphone system. The ANR audiometer (33) requires two inputs which are the left and right error microphone signals from the ANR audiometer headphones (32). The ANR audiometer then provides a single voltage signal to each of the two ANR headphones consisting of the control voltage summed with the audiometer test stimulus which has been calibrated to deliver the proper SPL to the subject for a given voltage output. This summation and calibration is performed inside the audiometer and thus is referred to as an integrated ANR audiometer. The ANR audiometry headphone arrangement required for this, the most complex type of ANR audiometer, is the simplest arrangement requiring a single input (actuator voltage signal) and single output (error microphone signal) for each of the two headphones.

FIG. 4b illustrates a slightly simpler configuration for the ANR audiometer, but requires a more complex configuration for the ANR audiometer headphones. The ANR audiometer (35), still performs the calibration of the audiometer signal in conjunction with the active noise control, but does not add the control signal to the calibrated audiometer test stimulus. (This may be done so that the audiometer can be used with other headphones that are not equipped with the capabilities of the ANR audiometer headphones). The outputs of the ANR audiometer headphones (34) are still each of the error signals but the inputs are now the left and right active control signals as well as the calibrated left and right test stimulus signals. The headphone architecture will now include an electronic summing junction (36) which will combine these two signals into a single voltage to drive a single actuator for each ear. (Recall that another possible embodiment in FIG. 1a provides for separate actuators for control and test signals, that is not excluded by this description). Although not explicitly shown in FIG. 4b, it is possible that the control output source and calibrated output source have different impedance values, a feature that will also require an impedance matching circuit included in the summing junction (36), easily realized with operational amplifiers.

FIG. 4c illustrates a final configuration for an integrated ANR audiometer without the feature of integrated audiometer signal calibration (38). Because of this, this embodiment of the ANR audiometer headphones (37) require additional hardware. The outputs of the headphones remain the same as in previous embodiments, and are the error microphone signals from each earphone. The inputs are also the same as described for FIG. 4b. However, since the calibration of the audiometer test signal is not being performed within the audiometer, the ANR audiometer headphones must account for the effects of the ANR on the test stimulus by providing a separate calibration means on the audiometer test stimulus. The method for this calibration differs for each test stimulus and is described in greater detail in the latter half of this description. The focus in this description is the external gain required on the audiometer test stimulus prior to summation (39) of the control and audiometer signals so that the proper SPL is delivered during testing. This external gain is realized as either an integral part of the ANR audiometry headphones (37) or a separate circuit connected to by the output of the ANR audiometer (38) and the input to the ANR audiometry headphone configuration (34) as shown in FIG. 4b.

In the above descriptions, the control mechanism configuration can vary widely. As previously stated, the focus is on the ANR audiometry headphone, its integration with ANR audiometers, and the calibration procedures required. One assumption has been implied throughout, which is that a control signal must be used to drive the actuator used in active noise control and that an error signal is used to update calculation of the control signal. In some control configurations (such as feedforward), another measure of the ambient noise is often used. This is a controller design issue and does not directly affect the ANR audiometry headphone design discussed herein. These assumptions remain valid throughout the following discussion of ANR audiometry headphones used in conjunction with retro-fit ANR audiometers.

Figure 5C:
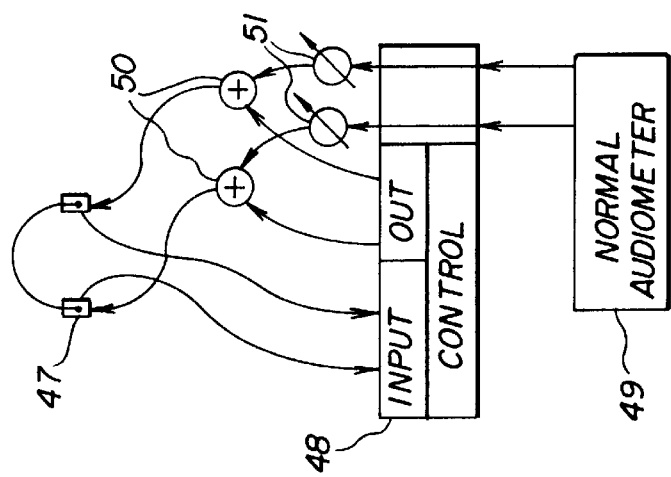
FIGS. 5a, 5b and 5c illustrate the same ANR headphone configurations as described in FIGS. 4a, 4b and 4c, respectively, but they assume that the ANR audiometer is a retrofit device as opposed to the integrated ANR audiometer illustrated in FIGS. 4a, 4b and 4c.
Figure 5B:
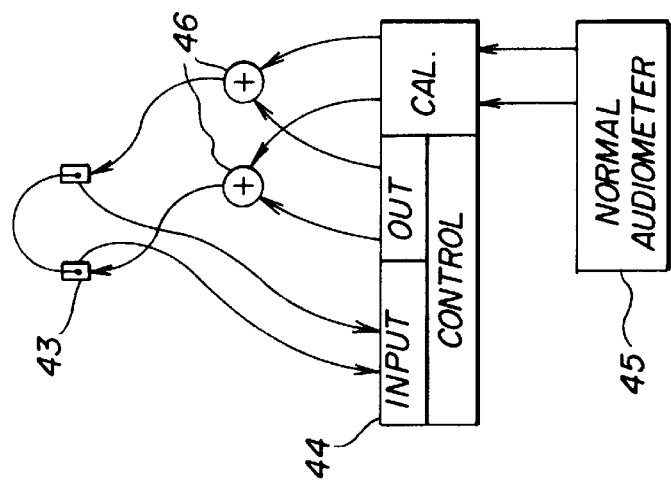
Figure 5A:
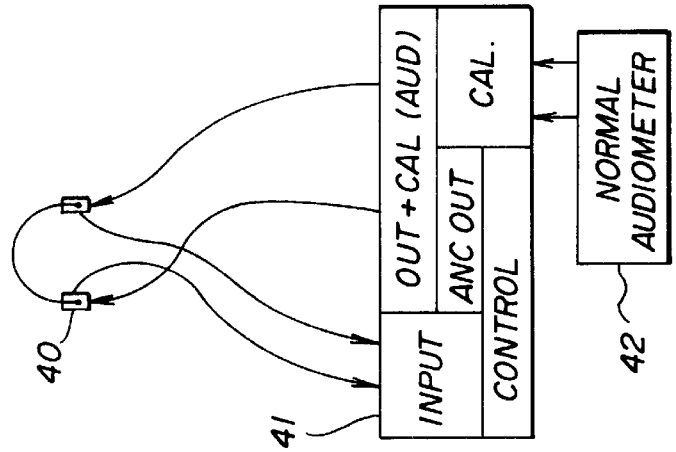

A retro-fit ANR audiometer is a device that can be attached to a standard screening or clinical audiometer to give it the same capabilities as a fully integrated ANR audiometer. Facilities that are desirous of including the benefits of ANR audiometry need not purchase an entirely new audiometer but can simply attach the retro-fit audiometer to the normal audiometer, connecting only the left and right signal outputs to the left and right retro-fit ANR device audiometer inputs. The ANR audiometry headphones that can be used with such a retro-fit device will depend on the construction of the device and are similar to those discussed in FIGS. 4a, 4b, and 4c. FIGS. 5a, 5b, and 5c illustrate three possible configurations for the ANR retro-fit device used with a standard audiometer. The retro-fit device (41) in FIG. 5a generates the two control outputs (left and right), calibrates the left and right audiometer signals, and sums the control signal and test stimulus within so that only two outputs are required. Therefore, as in FIG. 4a, the ANR audiometer headphones that will operate with this device require only two inputs, the left and right actuator driving signal. FIGS. 5b and 5c are identical to FIGS. 4b and 4c and accompanying explanations are not required. The only notable difference is that the ANR audiometry headphones connect with the retro-fit device rather than the audiometer itself. As before, the impedance switch may be required as part of the headphones, depending on the output impedance of the retro-fit device. It should also be noted that the impedance must also match between the audiometer and the retro-fit device, another application for the impedance switch. (This was not an issue for the integrated ANR audiometer because the hardware was designed together).

Before discussing more specific ways of integrating the calibration hardware (51) for the ANR audiometry headphones, several embodiments are described pertaining to the calibration procedure itself. The calibration method of standard audiometry headphones is specified in ANSI S3.6-1989 for supra-aural style cushions similar to the MX41/AR. An acoustic coupler specified by the National Bureau of Standards as type 9-A, mates a one inch microphone with the cushion, creating a volume of 6 cubic centimeters. This standard is intended to approximate the volume created when the earphones are placed on the average human ear, so that the sound pressure level at the eardrum can be known with some degree of repeatability.

Figure 6:
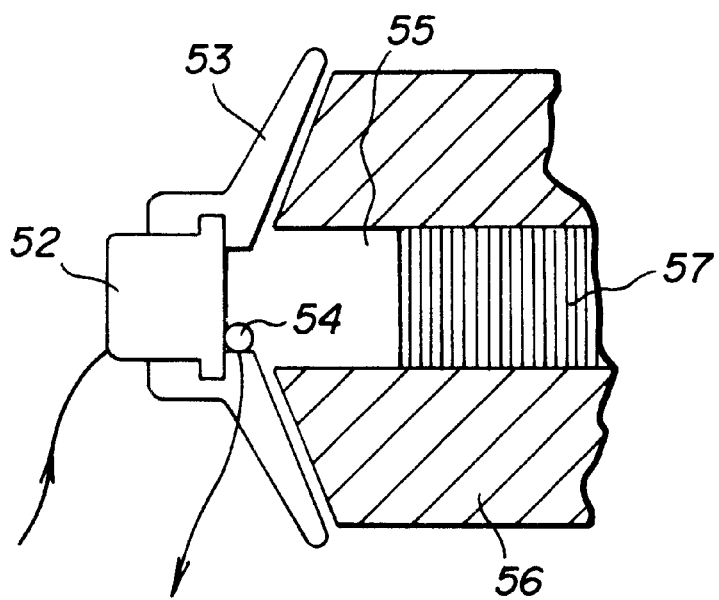
FIG. 6 illustrates a calibration configuration for the ANR headphone for audiometry that conforms to current standards for audiometer headphone calibrations.

The ANR audiometry headphones can be designed in such a way that this standardized calibration procedure can be adhered to without costly changes or modifications in standards. FIG. 6 illustrates this standard calibration process for one embodiment of the ANR audiometry headphone. The earphone (52) and cushion (53) styles shown are meant to depict the standard TDH type speaker coupled with the MX style cushion. This permits a calibration procedure that adheres to the standard, specifying a type 9-A acoustic coupler (56) creating a 6 cc volume (55) with a one inch microphone (57). The ANR audiometry headphone must include an acousto-electric transducer (54) to measure the noise under the earcup during operation. Typically this is a microphone that can be quite small. In FIG. 6, the microphone is shown as being integrated into the MX style cushion. This detail is critical in that the presence of the microphone does not reduce the volume of the cavity created during the calibration procedure. It is also important that the microphone be molded into the cushion so that no air gaps or leaks will reduce the passive performance of the cushion. Molding the electro-acoustic sensor into the ear cushion is only one of many possible arrangements that will permit the current calibration standard to be adhered to. The speaker could be slightly recessed inside its casing (52) to provide room for the microphone. This is a more significant design change, but one that would also meet the specification for calibration.

Figure 7:
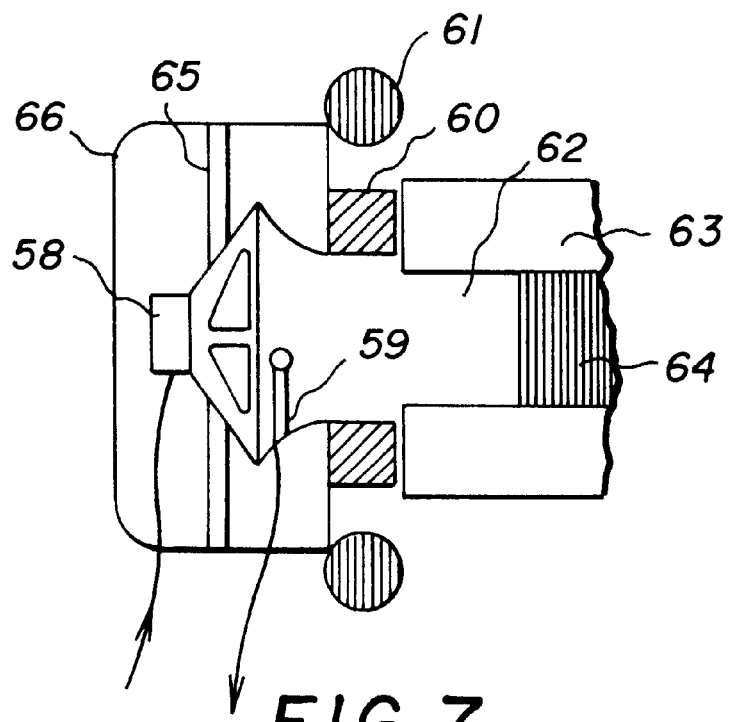
FIG. 7 illustrates an arrangement for a new ANR audiometer headphone and new calibration procedure which can be used to generate new standards for ANR audiometer headphone calibration.

As mentioned earlier, the TDH style speaker is not particularly well suited for active noise control due to its poor low frequency response. For this reason it is very important to consider other possible alternatives, whether they meet the current specification for audiometers or not. FIG. 7 illustrates only one of these possible alternatives for actuator, sensor, and passive control configurations. Although not drawn to scale, it is clear from the above description and FIG. 6, that this design will not meet the current specification for calibration of earphones. The speaker (58) is mounted as at (65) inside a circumaural cup (66) that contacts the subject's head at the cushion (61). A second inner cushion (60) will contact the user's pinna first, ensuring a seal with a known average volume and improving passive performance.

In this arrangement, the acousto-electric sensor can be more freely located in front of the speaker or closer to the user's ear canal. For each ANR audiometry headphone system design there is an optimum position for this sensor that offers the best perceived performance. The control performance is better when the microphone is closer to the speaker because of the reduced time delay. But as frequencies increase, the zone of silence around the sensor becomes smaller and the subject will have difficulty perceiving the effects without moving the microphone closer to the eardrum. One final criteria for the positioning of the sensor in the ANR audiometry headphone relates to the variability of the system dynamics for different test subjects. It is desirable to minimize this variability as it can adversely affect fixed gain control performance. Testing has shown that larger volumes (62) between the speaker and the pinna (where the sensor resides) provide less variability among users. Recall that the calibration standard requires a 6 cc volume that approximates the average volume present when the TDH and MX pair are placed on the subject's ear with a 4.5 N force headband. Better ANR performance can be achieved for a wider spectrum of the population if this volume is increased. This will clearly require a new calibration standard. While it is not the purpose of this embodiment to provide a completely new standard, it is intended to provide for a means by which this new standard can be created for a variety of ANR audiometry headphones.

In addition to an alternative arrangement for the actuator-sensor pair for ANR audiometry headphones, FIG. 7 also depicts one possible scheme which may be used to calibrate the new ANR audiometry headphones. A new acoustic coupler (63) which mates with the inner cushion (60) of the ANR audiometry headphones creates a specified volume (62) when sealed with a certain headband force. This volume shouldn't necessarily be 6 cc as long as the combination of the coupler and remaining acoustic volume is the average volume present when the headphone is placed on the human subject. For example, if the overall volume when placed on the average human ear is 12 cc, the coupler can be designed so that when a seal is made at the cushion (60), the overall volume (62) is also 12 cc. This will ensure that the SPL measured by the calibration microphone (64) is the same as that which is present at the eardrum, with the same degree of accuracy present in the current standard calibration scheme. A wide variety of ANR audiometry headphone arrangements can be designed as can calibrators for those headphones, without deviating from the intended embodiments described above.

Until now, the structure and design of the ANR audiometry headphones has been discussed in detail with little attention paid to the calibration process. The remainder of the preferred embodiments change focus slightly toward several new inventions related to the calibration of both standard audiometry headphones and ANR audiometry headphones. The first invention related to calibration of audiometry headphones can be implemented with either standard or the new ANR audiometry headphones; both embodiments are discussed in detail.

Pure tone audiograms report the hearing levels at different tonals throughout the spectrum for the test subject based on their direct feedback. The hearing levels are reported in dB but are a linear scale of the actual sound pressure level present at the ear canal. For example, a hearing level of 70 dB at 250 Hz is actually a sound pressure level close to 90 dB SPL. This also changes with test tone frequency and is based on the standard reference zero for a specified headphone. In order to ensure that the hearing level data reported is accurate (i.e. the measured hearing level is at a known SPL), each audiometry headphone must be calibrated before each use using the procedure as shown in FIG. 6. Most screening and clinical audiometers are equipped with calibration hardware built into the audiometer itself. In order to adjust the gain (calibration) for each tone, it is often necessary to physically remove components of the audiometer and to manually adjust gain levels either on the front panel controls or more complicated potentiometers. The invention discussed in the following paragraphs will permit calibration of either standard audiometer headphones or the new ANR audiometer headphones in a much more feasible manner, and in some embodiments, automatically.

FIG. 8a illustrates the general concept of the "in-line calibrator" for audiometer headphones (ANR and otherwise). The output of a standard pure tone audiometer (67) is connected by wire (68) to the input of the in-line calibrator (69), whose output (70) is the input of the headphone actuator (71). At this point, it is not required that the output of the audiometer be calibrated in any fashion. In general, the calibration procedure works as follows. The components are connected as shown in FIG. 8a and the headphone is placed on the acoustic coupler as shown in FIG. 6 and described in ANSI S3.6 1989. The audiometer is then set manually at the hearing level required for the calibration procedure (say 70 dB HL) for the first tone. The signal passes through the in-line calibrator which acts as a gain or an attenuator for that individual frequency before the tone is sent to the earphone and registered at the acoustic coupler microphone (57). If the measured SPL is too low according to the specification for the earphone being used (the levels are different for different earphone manufacturers), the accompanying gain of that tone, at that frequency is increased by the in-line calibrator. This process is repeated for each tone until all test frequencies register the correct SPL. The audiometry test is then conducted with the in-line calibrator still engaged, since it now adjusts the output of the audiometer to the proper SPL.

Before describing detailed components and embodiments of the in-line calibrator, consider the improvements in state-of-the-art audiometry testing offered by such a device. First, the calibration process no longer requires any modification to the calibration settings in the audiometer itself. If the in-line calibrator is implemented digitally, it will be easy to store many calibration settings for a variety of different audiometry headphones, eliminating the need for continual recalibration of multiple headphones. The in-line calibrator can work with any audiometer and any headphone combination so the clinician/audiologist does not need to become familiar with the different calibration processes of many different audiometers. This design will also lead to further embodiments which permit the audiometer calibration process to be completely automated.

Before describing further modifications to the in-line calibrator, several embodiments which detail its actual implementation are presented. The components shown in FIG. 8b represent one possible design implementation of the in-line calibrator in FIG. 8a. The input in FIG. 8a (68) is the same input shown in FIG. 8b as (72) and the components following (73)(74) can be viewed as a detail of (69). FIG. 8b illustrates a block diagram of a series of biquad op-amp circuits which create a filter design with the frequency response shown in FIG. 8c. Each series biquad segment has a complex pole and complex zero pair represented by the transfer function:

$$T(s) = \frac{s^2 + 2\xi_2\omega_{nz}s + \omega_{nz}^2}{s^2 + 2\xi_p\omega_{np}s + \omega_{np}^2}$$

Connecting many of these in series, each with lightly damped pole (75) and zero (76) pairs at increasing natural frequencies, the magnitude frequency response function shown in FIG. 8c results. (These complex pole/zero pairs can be built using five operational amplifiers by anyone well versed in the art, and is not described in detail here). If the natural frequencies of the poles are selected to be identical to each of the audiometry test tone frequencies, the damping ($\xi_p$) of each of the complex conjugate poles can be manually adjusted by changing certain resistor values in the biquad circuit to provide different gain values without affecting the other frequencies. The alternating complex zeros are included to prevent the high frequency magnitude from decreasing since audiometry testing occurs as high as 8000 Hz. The damping of the zeros is depicted as being quite small, but that is not required since their purpose is meant to counteract the high frequency effects of the poles. As mentioned earlier, the first biquad (73) will be designed so that the natural frequency of its poles corresponds to the first test tone frequency, say $F_1$. The second biquad (74) will have poles that correspond to $F_2$, and so on until all frequencies under test have been designed for. The calibration will occur as described above, by adjusting the damping of each of the complex poles when each corresponding frequency is under test. This represents one way in which the in-line calibrator can be implemented without the need for any type of switching mechanism, since all frequencies are calibrated in series and only one tone is under test at a time.

Figure 8D:
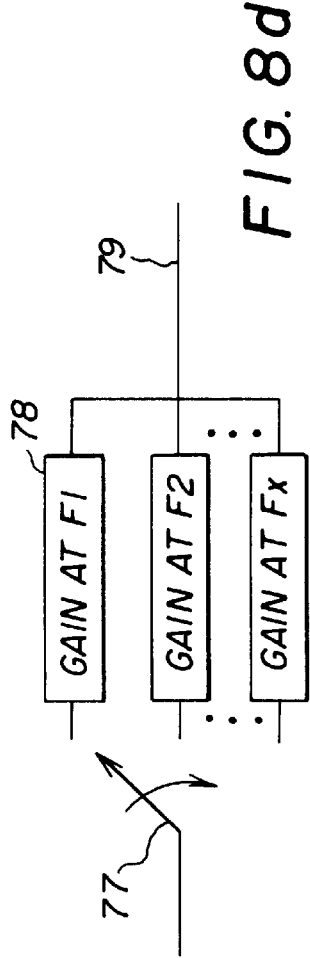
FIG. 8d illustrates the switching configuration for calibrating multiple non-simultaneous signals using the in-line calibration procedure.

Since only one frequency is tested at a time, another alternative for the design of the in-line calibrator is to incorporate a switch that selects a different gain for each frequency. FIG. 8d illustrates one such embodiment of the switching in-line calibrator. The input signal from FIG. 8a (68) is shown in FIG. 8d as the input to the switching mechanism (77). A bank of adjustable gain elements (78) (perhaps operational amplifiers if done in an analog format) is arranged in parallel such that only one element can simultaneously receive the input. The output (79) then goes directly to the audiometry headphone after the proper amplification. FIG. 8d illustrates the switch (77) as a manual device which can be switched along with the audiometer tone selector in order to engage the correct gain block. During calibration (for pure tone audiometry), the gain of each block can be independently adjusted and does not need to be a function of frequency. For example, if the first test frequency to be calibrated was 250 Hz, the first gain block would be selected and the gain of that amplifier would be adjusted so that the SPL measured at the calibration microphone matched the standard. Since only one frequency would be selected at a time from both the audiometer and the in-line calibrator, the gain blocks can be non-frequency dependent amplifiers. Once the gains for each test frequency and each of the respective gain blocks have been set, the audiometry test commences with the in-line calibrator switch used to select the proper frequency/gain. At this point, one might imagine that unless the audiometer frequency selector and the in-line calibrator switch (77) were connected, the potential for forgetting to adjust both switches after each test frequency is high. It is certainly not beyond the scope of the described embodiment to suggest connecting the in-line calibrator switch with the audiometer frequency selector. However, another aspect of this invention will automatically perform this task.

Figure 8E:
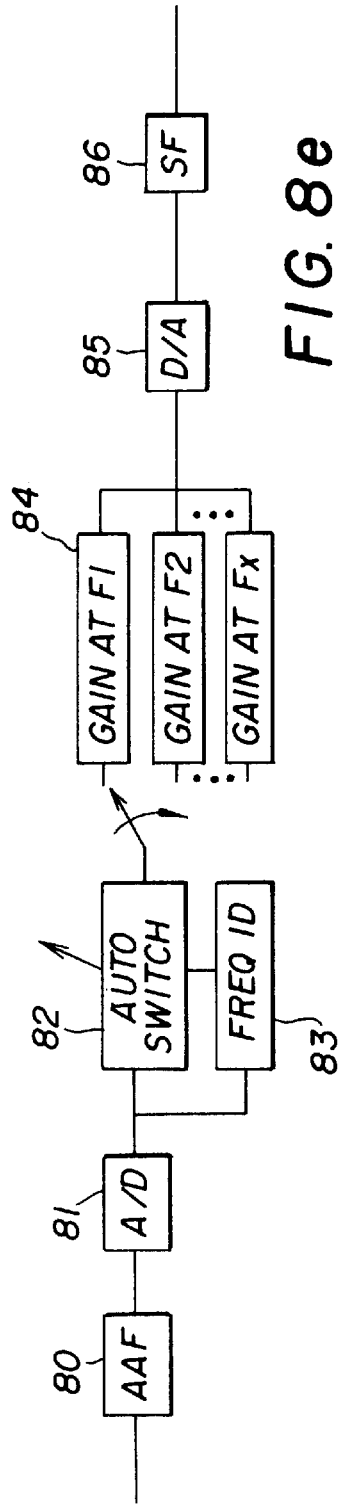
FIG. 8e illustrates one arrangement of a non-manual digital switching system for selecting different gains for different non-simultaneous audiometer test signals.

The switching in-line calibrator of FIG. 8d has two primary components: the switch itself, and the parallel gain bank. The gain bank can be implemented using operational amplifiers or can be a series of adjustable digital gains. For the latter, an anti-alias filter, sampling mechanism and digital-to-analog conversion is required for the audiometer test stimulus. If the digital implementation is adopted, a structure such as that which is shown in FIG. 8e could be realized. In this embodiment, the manual switch has been replaced by a method for automatically determining the input frequency and selecting the proper calibration gain block. Each gain block amplification is still set manually but the selection of the gain block during calibration and during test is done automatically. The input to the in-line calibrator (68) is anti-alias filtered (80), sampled (81), delivered to the automatic switching mechanism (82), which is controlled by the frequency identification algorithm (83). The automatic switch then selects the proper gain block (84) which receives the sampled test stimulus and amplifies or attenuates it before it is sent to the headphone (71) after the digital to analog conversion (85) and the smoothing filtering (86). During calibration, the automatic switch simply selects the gain block that is associated with the test stimulus frequency and connects the input signal to the input of the selected gain block. The gain for that block is then manually adjusted in the software algorithm until the correct SPL is registered for a certain HL being delivered by the audiometer. During testing, the automatic switch will again select the proper gain block for the frequency under test and modify the signal according to the gain set during the calibration procedure.

There are many possible ways in which the automatic switch (82) can be controlled (83) and made to select the correct gain block (84). Only one simplified method is described here. The frequency identification (83) portion of FIG. 8e represents a software algorithm that instructs the automatic switch to select the correct gain block that is associated with the input frequency. In order to do this, the algorithm must quickly decide what the frequency is of the incoming waveform and move the switch accordingly. To accomplish this a fast Fourier transform (FFT) is performed on the input signal and the relative powers in the frequency bins known to be centered on test stimulus frequencies are examined. If one is suddenly higher than another, the automatic switch is instructed to engage the gain block associated with that frequency. For example, some common audiometry test stimulus frequencies include 125 Hz, 250 Hz, and 500 Hz. (There are many others higher in frequency but these will serve the purpose for this explanation). Assuming the 250 Hz test tone was turned on at the audiometer and the input signal to the in-line calibrator was transformed to the frequency domain as part of the frequency identification algorithm. Now the signal power in the frequency bins centered on 125 Hz, 250 Hz, and 500 Hz can be compared to find that the power in the 250 Hz bin is highest when the tone is on, forcing the automatic switch to select a gain block. It is important to note that the embodiment for the automatic switch (82) itself, is actually part of a software code that makes a decision as to which gain to choose, rather than an actual hardware switch. If desired, however, the frequency identification and automatic switch can also be realized using standard analog and digital hardware such as transistor circuits for switching, voltage controlled amplifiers, and FFT integrated circuits. The calibration and testing process for this embodiment of the in-line calibrator are identical to the previous descriptions, with the exception that the gain blocks are automatically selected by the automatically controlled switch. The gain set for each gain block is still manually performed based on the measured SPL in the calibrator. Further novel aspects of this invention are described which show how the configuration will automate the entire calibration process including gain set.

Figure 9:
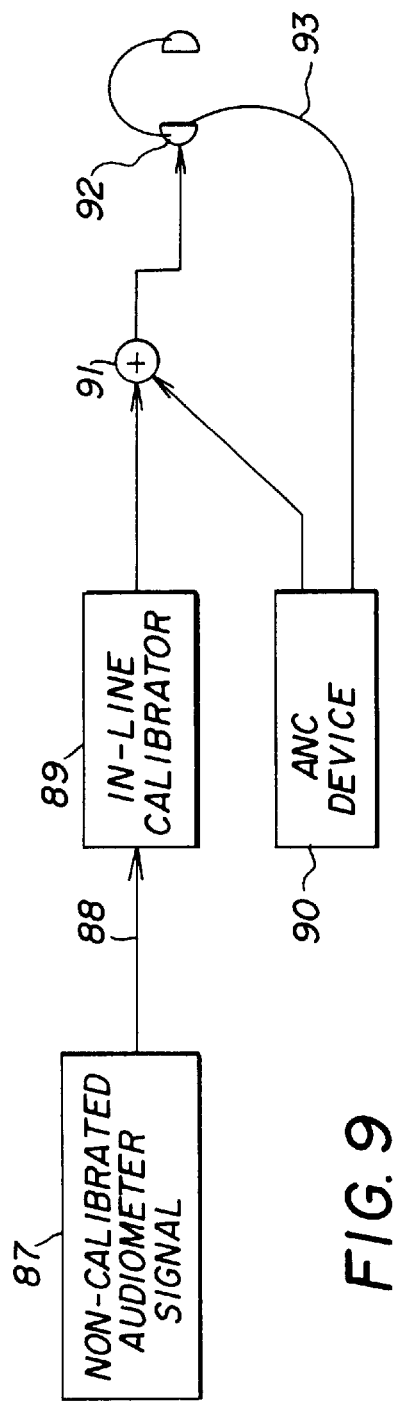
FIG. 9 illustrates how the in-line calibration procedure will apply to the ANR audiometer headphones, as opposed to the standard audiometer headphones in FIGS. 8a through 8e.

The above descriptions for the in-line calibrator focus on applications to standard audiometry headphones. Since one of the primary focus points for this patent is the ANR audiometry headphones, it is critical to understand how the in-line calibrator invention can be used in conjunction with these new headphones. FIG. 9 illustrates just this integration. As before, the non-calibrated audiometer signal (87) is delivered (88) from any audiometer into the in-line calibration hardware (89). Referring back to FIGS. 1b, 4, and 5, recall that there are many configurations for the ANR audiometry headphones input signals including multiple actuators, single actuators with single inputs, with dual inputs and with externally calibrated dual inputs. (All configurations of the ANR audiometry headphones require an output for each ear in the form of an acousto-electric transducer). Also note in FIGS. 4c and 5c that the calibration (51) of the audiometer signal is depicted in the same format as the in-line calibrator embodiments described above. This is identical in structure to the embodiment shown in FIG. 9. The ANR audiometry headphones (92) shown in FIG. 9 are the same structure/embodiment as depicted in FIGS. 4c and 5c except that the calibration method is in the form of the in-line calibrator in conjunction with a standard audiometer (as opposed to an integrated ANR audiometer or a retrofit device). This structure shown in FIG. 9 incorporates a means for adding (91) the calibrated audiometer signal to the output of the ANR device (90) in the same manner as described in FIGS. 4c and 5c in (39) and (50). During calibration, the ANR headphone is placed on the appropriate acoustic coupler with the ANR device operating. This is required since most ANR methods will affect the audiometer signal because it appears as a disturbing noise that the control will try to reduce. So in this format, the in-line calibrator serves a dual purpose: adjusting the audiometer signal to deliver the correct SPL for a given HL and correcting for the affects of the ANR device.

In the case where two actuators are used as in FIG. 1b, the summing junction (91) (50) or (39) is not required. The output of the inline calibrator goes directly to the input of one actuator while the output of the ANR device goes directly to the input of the other actuator. As mentioned earlier, the in-line calibration scheme must be performed while the ANR device is operational because the test stimulus "appears" as a disturbance to the ANR. FIGS. 4a, 4b, 5a, and 5b represent further embodiments of the ANR audiometry headphones, but do not require the in line calibration technique, per se. In FIGS. 4a and 4b, the calibration is depicted as part of the ANR integrated audiometer. FIGS. 5a and 5brepresent the retrofit device which is separate from the normal audiometer, but also has a calibration scheme. In some sense this embodiment of the retrofit audiometer can be considered as a form of in-line calibration for the ANR audiometry headphones.

Figure 10A:
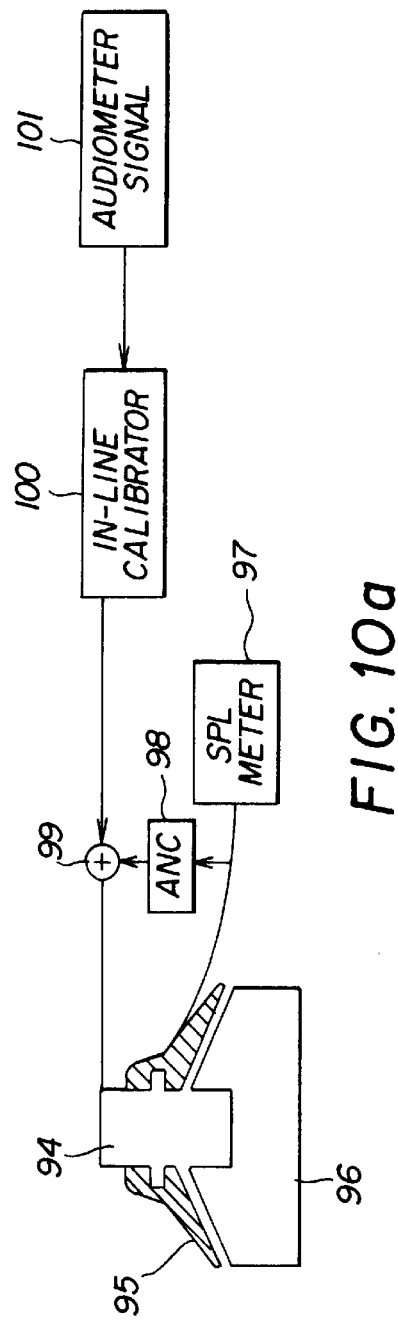
FIG. 10a illustrates an arrangement where the calibration procedure has been established to permit the use of the ANR error microphone to be used as the SPL reference incorporating both the ANR device and the in-line calibration procedure.

The final two aspects of this invention focus on innovations in the calibration method for ANR audiometry headphones but which can also be applied to standard audiometric headphones, with proper modifications. By way of explanation, recall that the ANR audiometry headphones must be equipped with a sensor (acousto-electric transducer) for measuring ambient noise inside the earcup and recall that during calibration of standard audiometric headphones, the actuator/cushion pair is placed on an acoustic coupler equipped with a microphone for measuring the SPL occurring inside a simulated human ear for a given HL setting on the audiometer. Now, since the ANR audiometry headphones come equipped with a microphone, FIG. 10a depicts one possible way that this microphone can be used in place of the calibration microphone, significantly reducing cost for calibration equipment. The earphone (94) and cushion (95) (also shown as (52) and (53) in FIG. 6) are placed on a new type of acoustic coupler (96). This coupler seals the cushion in the same manner as the human pinna (and the traditional acoustic coupler), but has no calibration microphone. It is simply a closed volume of 6 cubic centimeters when the earphone is placed upon it. Also inside this volume is the error microphone for the ANR audiometry headphones. This microphone is now used as the calibration microphone. The important assumption to be made is that the SPL measured at the error microphone is the same as would be measured by a calibration microphone at the bottom of the acoustic coupler. For such a small volume in an enclosure, this is a valid assumption. (There is uncertainty as to whether the standardized acoustic coupler microphone measured SPL actually represents the SPL at the eardrum of a test subject—it is merely a way of providing a uniform calibration across the population. So it is unimportant whether the ANR error microphone measured SPL exactly represents the SPL at the eardrum, as long as a uniform calibration procedure exists among all ANR audiometry headphones).

The calibration process for the ANR audiometry headphone using the error microphone as the calibration microphone proceeds as with the other in-line calibration procedures. The error microphone is used to monitor (97) the SPL in the enclosure as well as provide a sensing means for the ANR controller (98). A summing junction (99) is required to combine the noise control signal with the calibrated audiometer signal, if only one actuator is used. The in-line calibrator (100) can take on any of the aforementioned embodiments without loss of generality.

During calibration of the system in FIG. 10a, the experimenter adjusts the audiometer signal (101) to a certain HL that should have a SPL as stated in the standards established for that specific headphone. The experimenter then views the SPL meter (97) and adjusts the calibrator (100) until the measured SPL matches the value specified in that standard. This process is repeated until all frequencies are calibrated. In this arrangement, the human acts as the feedback loop in controlling the SPL with the calibrator. Since the process already requires an electronic measurement of the SPL inside the earphone during calibration, this signal can be used electronically to automatically update the calibrator for each frequency, removing the human from the "loop".

Figure 10B:
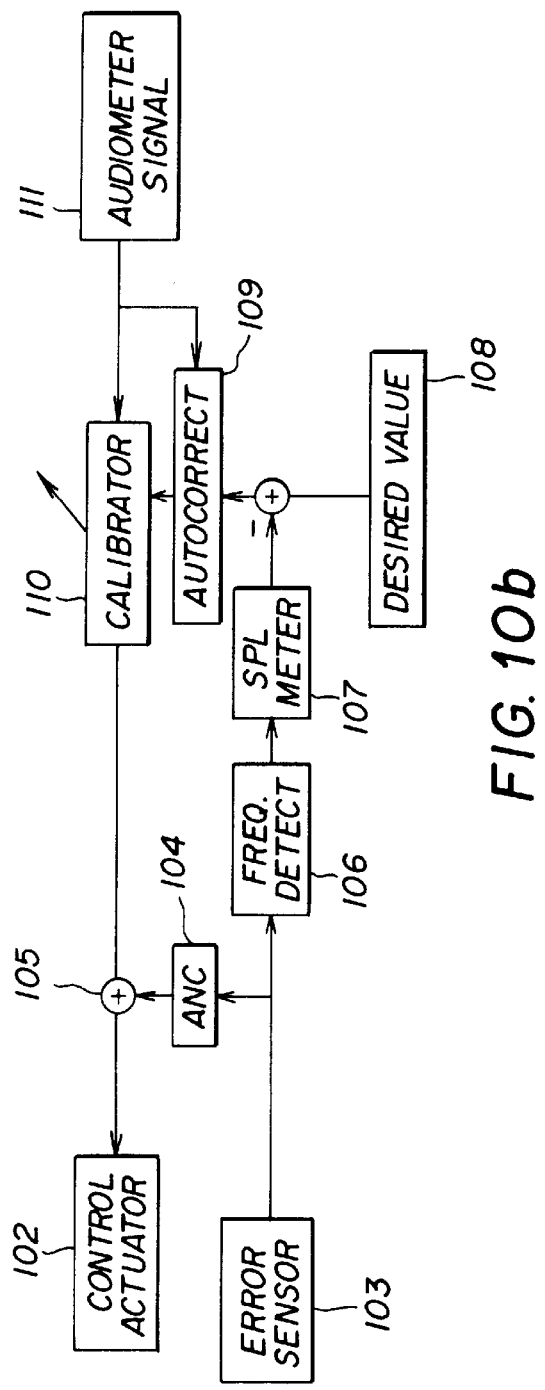
FIG. 10b shows an embodiment for an automatic calibration procedure using the ANR error microphone.

FIG. 10b depicts one possible embodiment for this process of automatic ANR audiometer headphone calibration. The control actuator (102) is the same as the headphone depicted in FIG. 10a, only in block diagram form. The error sensor (103) for ANR audiometry headphone calibration acts as both the error sensor for the ANR device and the calibration microphone for the calibration process. Accordingly the error signal is delivered to the ANR device (104)

and the first stage of the automatic calibration scheme which is a frequency detector (106). The combination of the frequency detector and the SPL meter (107) will automatically determine what the test frequency being delivered by the audiometer (111) is, as well as the SPL inside the calibration fixture. Once the current test frequency and its SPL is known, a database of the proper SPL values for specific earphones and specific HL's is used to determine the desired value (108) for the current calibration. This desired value is then compared to the actual value to generate (109) another type of "error" signal that is used to update the calibrator (110). In general, these tasks are most easily performed in software so the desired values and calibration values for certain headphones can be stored in electronic memory.

The autocorrect procedure (109) can be physically realized in many formats. The one described here is in the form of the popular LMS algorithm for feedforward control. The LMS algorithm updates the filter weights of an adaptive filter so that the a mean squared error signal is minimized. The error signal is generated by taking the difference of the actual measured value (the measured SPL) and the desired signal (which in this case is the standard SPL value for a given headphone and HL) and minimizing the error between them adjusting the filter weights. One unique element of the adaptive filter design for this application is the fact that the signal to control has no AC component. Therefore the adaptive filter needs only one DC weight to update the filter. Because the adaptive filter and the LMS require only a single weight to accomplish the desired goal, this method can be implemented with analog electronics as well as a digital signal processor. The analog version of the LMS is slightly different from the discrete version in that it requires an integrator rather than a summer. To explain this in terms of the ANR audiometer headphones, reconsider FIG. 10b. The autocorrect element (109) is actually the LMS algorithm (analog or digital) with the difference from the SPL meter and the desired value acting as the error signal. The input to both the LMS and the adaptive filter (which for the audiometer system is the automatic calibrator (110)) is the output of the audiometer (111). Once the error has been minimized sufficiently (within a tenth of a dB), the converged adaptive weight can be stored in memory for use during audiometry testing. (Convergence can be stopped at any time by setting the convergence parameter $\mu$ to zero). The uniqueness lies in the autocorrect procedure and any scientist well versed in the art of adaptive control can implement the automatic calibration system given the information provided above.

The previous descriptions assume that the audiometer test stimulus frequency is adjusted manually. Unless the manual adjust on the audiometer is coupled to the frequency detection (106) method, the frequency detection must be performed in hardware or software. The same problem is encountered with the desired value (108) input in that the desired value is frequency dependent and thus depends on the current test stimulus frequency. In order to completely automate the entire calibration process, the audiometer (111) needs to work in conjunction with the frequency detection (106) and the desired value (108). For example, the audiometer is capable of operating in two modes, automated calibration mode and test mode. (Test mode is self explanatory). The automated calibration mode runs through every test frequency automatically adjusting the calibration gains for each frequency. If the frequency detection element and the desired value element "know" what frequency the audiometer is generating, there is no need for any special detection hardware or software. If the audiometer begins with 125 Hz, that value is passed directly to the frequency detection element so the SPL at 125 Hz can be monitored, and the desired value for the SPL at 125 Hz for a given earphone. (Recall that HL is a function of SPL and so the desired value will also depend on the currently selected HL. Unless the automation process is coupled to the audiometer as described here, the HL level will also need to be a manual input for the less-automated approach described in the preceding paragraphs).

Finally, the automatic calibration procedures described above were related directly to the ANR audiometer headphones invention. The use of the error microphone from the ANR audiometry headphones, in the calibration process (manual or automated) can only be done with the ANR audiometry headphones since standard audiometry headphones do not require such an error sensor. This is why the calibration process for standard audiometry headphones requires a calibration fixture (acoustic coupler) equipped with a calibration microphone. Although the automatic calibration procedure was initially presented as an option for the ANR audiometer headphones utilizing the error microphone, there is no reason why standard headphones cannot be calibrated using this automatic procedure and the calibration microphone. Revisiting FIG. 10b, the only modifications required for implementing the automatic calibration method for standard audiometric headphones is to remove the ANR device (104) and thus the adding circuit (105), and to replace the ANR error sensor (103) with the calibration microphone. This device can now be used to automatically calibrate any standard audiometric headphone system whose standard values for SPL at given HL levels are known. All modifications, algorithms and embodiments described for the ANR audiometry headphone automatic calibration procedure will still apply to this invention for standard audiometric headphone calibration.

Many new innovations and unique aspects of this invention have been discussed in the description of the preferred embodiments presented above. In general they can be divided into two major categories, each with significant subcategories. The first main category presented discussed the ANR audiometry headphones. The general structure and primary differences with standard audiometry headphones were presented first. Next, various physical architectures which included passive control, actuator placement and type, and sensor placement were discussed. Configurations of the inputs and outputs of the ANR audiometer headphones were presented with respect to different configurations of an integrated ANR audiometer system and a retrofit ANR audiometer system. Current standards for calibration of standard audiometry headphones versus the calibration procedures designed for the ANR audiometry headphones were explained in terms of the physical plant architecture. This discussion led to the next set of inventions regarding the calibration process of both standard audiometry headphones and the new ANR audiometry headphones. The new in-line calibrator was described, as were many possible implementations for pure-tone audiometry. Manual, automatic, analog, and digital realizations of the invention were described in detail. The in-line calibrator can be used with both the standard audiometer headphones as well as the ANR audiometer headphones, a configuration that was described next. A cost saving method for calibrating ANR audiometer headphones utilizing the error sensor built into the system was then presented. Finally, methods for semi-automatic and fully automated calibration of both standard audiometer headphones and ANR audiometer headphones were explained in detail, offering several alternatives for practical implementation.

It will be obvious to those of ordinary skill in the art to make many changes and modifications to the invention without departing from the scope of the appended claims.

What is claimed is:

1. An active noise reduction headphone system, comprising a standard geometrical design for the earphone and a cavity volume of known proportion, and greater than 6 cc upon interface to an audiometry headphone calibration device, for use in audiometry testing, the improvement further comprising, an acoustic-electric sensing means, and an electro-acoustic transducing means, wherein said sensing means and transducing means are used cooperatively in conjunction with an audiometric testing device for determining the hearing acuity of a test subject.

2. An improvement as in claim 1 wherein said sensing means constitutes at least one microphone and said actuation means is at least one speaker.

3. An improvement as in claim 2 wherein said headphone system includes additional passive noise control measures for improving high frequency noise-control performance where said passive noise control measures include a circumaural seal around the user's ear.

4. An improvement as in claim 3 wherein said headphone system uses an MX style industry standard audiometry cushion that incorporates said sensing means to create an ANR audiometry headphone system.

5. An improvement as in claim 1 wherein said headphone system is configured to meet the ANSI S3.6 standard.

6. An improvement as in claim 1 wherein said hearing acuity testing device is either a standard audiometer incapable of ANR audiometry testing, an ANR audiometer, or a retrofit ANR audiometer device that is used in conjunction with a standard audiometer.

7. An improvement as in claim 1 wherein said headphone system includes a summing junction for combining the active noise reduction signal and the audiometry test signal.

8. An improvement as in claim 6 wherein said headphone system includes a means for selecting different impedance values for use with different audiometric testing devices.

9. An improvement as in claim 1 wherein the cavity volume of known proportions is created by interface to the calibration device as specified by ANSI standard S3.6.

10. An improvement as in claim 1 wherein the geometry of the seal between the headphone and the user conforms to ANSI Standard S3.6.

11. An improvement as in claim 3 wherein said cavity volume constitutes an inner volume adjacent to said transducer and including the inner volume of the test subject's ear.

12. An improvement as in claim 1 wherein said transducing means is also used to deliver the audiometric test stimulus.

* * * * *

UNITED STATES PATENT AND TRADEMARK OFFICE
CERTIFICATE OF CORRECTION

| | | |
|---|---|---|
| PATENT NO. | : 6,532,296 B1 | Page 1 of 1 |
| APPLICATION NO. | : 09/123973 | |
| DATED | : March 11, 2003 | |
| INVENTOR(S) | : Michael Allen Vaudrey and William Richard Saunders | |

It is certified that error appears in the above-identified patent and that said Letters Patent is hereby corrected as shown below:

Column 1, line 4, insert the following section title and paragraph before the section entitled "Field of the Invention":

--GOVERNMENT RIGHTS

This invention was made with Government support under contract F41624-97-C-2005 awarded by the Department of the Air Force. The Government has certain rights in this invention. The U.S. Government has a paid-up license in this invention and the right in limited circumstances to require the patent owner to license others on reasonable terms as provided by the terms of contract F41624-97-C-2005 awarded by the Department of the Air Force.--

Signed and Sealed this

Eighth Day of December, 2009

David J. Kappos
*Director of the United States Patent and Trademark Office*